(12) United States Patent
Abedian et al.

(10) Patent No.: US 11,446,072 B2
(45) Date of Patent: Sep. 20, 2022

(54) SELF-RETAINING NAIL TO INSERTION HANDLE INTERFACE

(71) Applicant: DEPUY SYNTHES PRODUCTS, INC., Raynham, MA (US)

(72) Inventors: Reza Abedian, Etziken (CH); Christof Dutoit, Etziken (CH); Markus Buettler, Mumliswil (CH); Henri Defossez, Neuchatel (CH); Simon Wampfler, Lohn-Ammannsegg (CH); Alain Saurer, Neuchatel (CH); Remo Pfaff, Urtenen-Schönbühl (CH); Hans Bernhard, Liebefeld (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 15/729,256

(22) Filed: Oct. 10, 2017

(65) Prior Publication Data
US 2019/0105093 A1    Apr. 11, 2019

(51) Int. Cl.
*A61B 17/72*      (2006.01)
*A61B 17/88*      (2006.01)
(Continued)

(52) U.S. Cl.
CPC ...... *A61B 17/8872* (2013.01); *A61B 17/1725* (2013.01); *A61B 17/72* (2013.01);
(Continued)

(58) Field of Classification Search
CPC ...... A61B 17/1717–1725; A61B 17/8875–921
See application file for complete search history.

(56) References Cited

U.S. PATENT DOCUMENTS 2,312,869 A * 3/1943 Boyer ............... A61B 17/8891
                                                   81/438
4,911,153 A * 3/1990 Border ............... A61B 17/1721
                                                  606/64
(Continued)

FOREIGN PATENT DOCUMENTS

DE      102007016459 A1    10/2008
DE      102007016459 B4    4/2010
(Continued)

*Primary Examiner* — Eduardo C Robert
*Assistant Examiner* — Steven J Cotroneo
(74) *Attorney, Agent, or Firm* — BakerHostetler

(57) ABSTRACT

An implant insertion assembly including an insertion handle extending from a proximal end to a distal end, the distal end including a recessed portion, an outer wall of the recessed portion having a first shape about a perimeter thereof and including an engagement mechanism. The implant insertion assembly also includes an implant extending from a distal end to a proximal end including an opening configured to receive the recessed portion of the insertion handle, the opening having a second shape configured to mechanically interlock with the outer wall of the recessed portion when the recessed portion is inserted therein to transmit torque from the insertion handle to the implant, the proximal end including a receiving structure in a wall thereof, the receiving structure being positioned and oriented to receive the engagement mechanism to removably lock the insertion handle to the implant in the axial direction.

24 Claims, 10 Drawing Sheets

(51) Int. Cl.
*A61B 17/92* (2006.01)
*A61B 17/17* (2006.01)
*A61B 17/00* (2006.01)
*A61B 90/00* (2016.01)

(52) U.S. Cl.
CPC .. *A61B 17/921* (2013.01); *A61B 2017/00469* (2013.01); *A61B 2017/00477* (2013.01); *A61B 2090/0808* (2016.02)

(56) References Cited

U.S. PATENT DOCUMENTS

| | | | |
|---|---|---|---|
| 5,312,406 A | 5/1994 | Brumfield | |
| 5,507,211 A * | 4/1996 | Wagner | A61B 17/8875 81/125 |
| 5,549,610 A | 8/1996 | Russell et al. | |
| 5,620,445 A | 4/1997 | Brosnahan et al. | |
| 5,855,579 A | 1/1999 | James et al. | |
| 5,935,127 A | 8/1999 | Border | |
| 6,120,504 A | 9/2000 | Brumback et al. | |
| 6,123,708 A | 9/2000 | Kilpela et al. | |
| 6,126,661 A | 10/2000 | Faccioli et al. | |
| 6,214,013 B1 | 4/2001 | Lambrecht et al. | |
| 6,221,074 B1 | 4/2001 | Cole et al. | |
| 6,299,648 B1 | 10/2001 | Doubler et al. | |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,461,360 B1 | 10/2002 | Adam | |
| 6,524,313 B1 | 2/2003 | Fassier et al. | |
| 6,855,146 B2 | 2/2005 | Frigg et al. | |
| 6,932,818 B2 | 8/2005 | Behrens | |
| 7,018,380 B2 | 3/2006 | Cole | |
| 7,041,104 B1 | 5/2006 | Cole et al. | |
| 7,144,399 B2 * | 12/2006 | Hayes | A61B 17/1725 606/98 |
| 7,455,673 B2 | 11/2008 | Gotfried | |
| 7,670,340 B2 | 3/2010 | Brivio et al. | |
| 7,763,023 B2 | 7/2010 | Gotfried | |
| 7,776,038 B2 | 8/2010 | Prien | |
| 7,815,647 B2 * | 10/2010 | Volzow | A61B 17/921 606/99 |
| 7,842,036 B2 | 11/2010 | Phillips | |
| 7,867,231 B2 | 1/2011 | Cole | |
| 7,914,532 B2 | 3/2011 | Shaver et al. | |
| D638,125 S | 5/2011 | Velikov | |
| D638,126 S | 5/2011 | Velikov | |
| 8,137,348 B2 | 3/2012 | Gotfried | |
| 8,152,807 B2 * | 4/2012 | Edwards | A61B 17/1725 606/62 |
| 8,157,803 B1 | 4/2012 | Zirkle, Jr. et al. | |
| 8,241,286 B2 * | 8/2012 | Metzinger | A61B 17/1703 606/104 |
| 8,353,910 B2 | 1/2013 | Dell'Oca | |
| 8,409,205 B2 | 4/2013 | Yang et al. | |
| 8,449,544 B2 | 5/2013 | Grusin | |
| 8,540,714 B2 * | 9/2013 | Gordon | A61B 17/1725 606/62 |
| D693,470 S | 11/2013 | Fagan | |
| 8,632,543 B2 | 1/2014 | Metzinger et al. | |
| 8,652,136 B2 | 2/2014 | Yang et al. | |
| 8,668,695 B2 | 3/2014 | Schwammberger et al. | |
| 8,679,121 B2 | 3/2014 | Czartoski et al. | |
| 8,734,448 B2 | 5/2014 | Thakkar | |
| 8,758,345 B2 | 6/2014 | Sidebotham | |
| 8,790,343 B2 | 7/2014 | McClellan et al. | |
| 8,834,469 B2 | 9/2014 | Watanabe et al. | |
| 8,906,023 B2 | 12/2014 | Matityahu et al. | |
| 9,017,407 B2 * | 4/2015 | Donner | A61F 2/30988 623/17.11 |
| 9,044,283 B2 | 6/2015 | Simon | |
| 9,072,552 B2 | 7/2015 | Simon et al. | |
| 9,155,582 B2 * | 10/2015 | Felder | A61B 17/72 |
| 9,220,544 B2 | 12/2015 | Matityahu et al. | |
| 9,308,031 B2 * | 4/2016 | Elghazaly | A61B 17/725 |
| 9,320,551 B2 | 4/2016 | Frank et al. | |
| 9,358,049 B2 | 6/2016 | Simon et al. | |
| 9,408,645 B2 | 8/2016 | Graca et al. | |
| 9,433,449 B2 | 9/2016 | Vega et al. | |
| 10,251,691 B2 * | 4/2019 | Hedgeland | A61B 17/1721 |
| 2008/0009873 A1 | 1/2008 | Yacoubian | |
| 2009/0318926 A1 * | 12/2009 | Christie | A61B 17/1725 606/96 |
| 2009/0326541 A1 * | 12/2009 | Metzinger | A61B 17/1725 606/98 |
| 2011/0098715 A1 | 4/2011 | Laubert et al. | |
| 2011/0306984 A1 | 12/2011 | Sasing | |
| 2012/0215232 A1 * | 8/2012 | Olsen | A61B 17/1728 606/139 |
| 2012/0221005 A1 | 8/2012 | Corneille et al. | |
| 2014/0052132 A1 | 2/2014 | Matityahu et al. | |
| 2014/0330274 A1 | 11/2014 | Matityahu et al. | |
| 2014/0378973 A1 | 12/2014 | Mueckter et al. | |
| 2015/0112345 A1 | 4/2015 | Boraiah | |
| 2015/0182266 A1 | 7/2015 | Jakob et al. | |
| 2015/0257807 A1 | 9/2015 | Strnad et al. | |
| 2016/0113757 A1 * | 4/2016 | Diduch | A61B 17/8872 606/104 |
| 2016/0256202 A1 | 9/2016 | Halder | |
| 2017/0042600 A1 | 2/2017 | Ross | |

FOREIGN PATENT DOCUMENTS

| | | |
|---|---|---|
| DE | 102013113135 | 5/2015 |
| EP | 1053718 A1 | 11/2000 |
| EP | 1495733 A2 | 1/2005 |
| EP | 1654993 A1 | 5/2006 |
| EP | 1199995 B1 | 9/2007 |
| EP | 1859751 A1 | 11/2007 |
| EP | 1867294 A2 | 12/2007 |
| EP | 1654993 B1 | 1/2008 |
| EP | 1053718 B1 | 7/2008 |
| EP | 1974681 A2 | 10/2008 |
| EP | 1974681 B1 | 6/2010 |
| EP | 1495733 B1 | 9/2010 |
| EP | 1859751 B1 | 9/2010 |
| EP | 1867294 B1 | 9/2010 |
| EP | 2755580 B1 | 9/2011 |
| EP | 2109404 B1 | 1/2012 |
| EP | 1948049 B1 | 5/2012 |
| EP | 2341854 B1 | 9/2013 |
| EP | 2712562 A1 | 4/2014 |
| EP | 2349040 B1 | 8/2014 |
| EP | 2783649 A1 | 10/2014 |
| EP | 2712562 B1 | 7/2015 |
| EP | 2672909 B1 | 10/2015 |
| EP | 2950729 | 12/2015 |
| EP | 2783649 B1 | 5/2016 |
| EP | 2672910 B1 | 7/2016 |
| GB | 2445346 A | 7/2008 |
| GB | 2445346 B | 3/2011 |
| WO | 2000076414 A1 | 12/2000 |
| WO | 2007048038 A2 | 4/2007 |
| WO | 2008094407 A1 | 8/2008 |
| WO | 2008/122446 | 10/2008 |
| WO | 2010014694 A1 | 2/2010 |
| WO | 2010043380 A1 | 4/2010 |
| WO | 2012107056 A1 | 8/2012 |
| WO | 2012107226 A1 | 8/2012 |
| WO | 2013037386 A1 | 3/2013 |
| WO | 2014/174486 | 10/2014 |
| WO | 2015106319 A2 | 7/2015 |
| WO | 2016042148 A1 | 3/2016 |
| WO | 2016151611 A1 | 9/2016 |

* cited by examiner

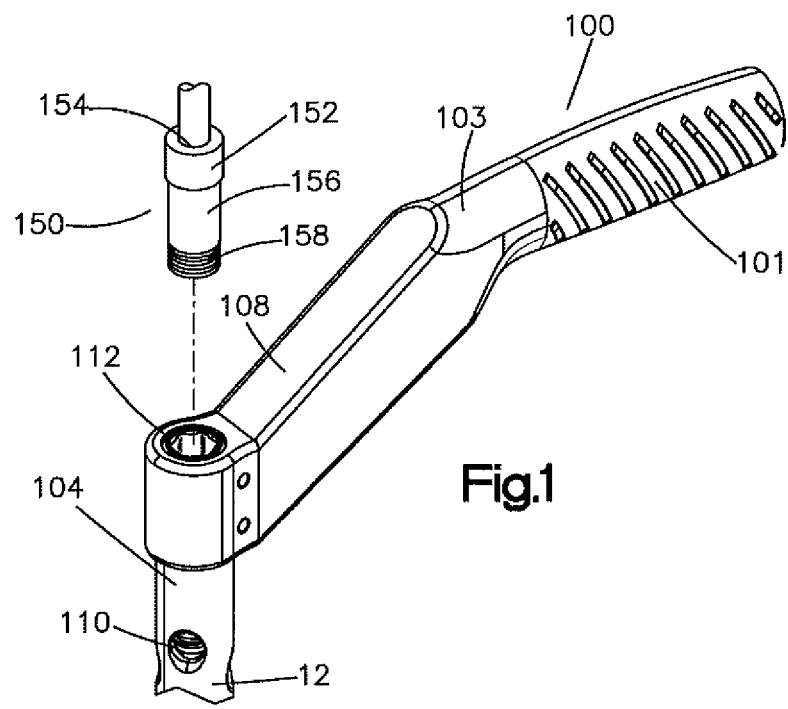
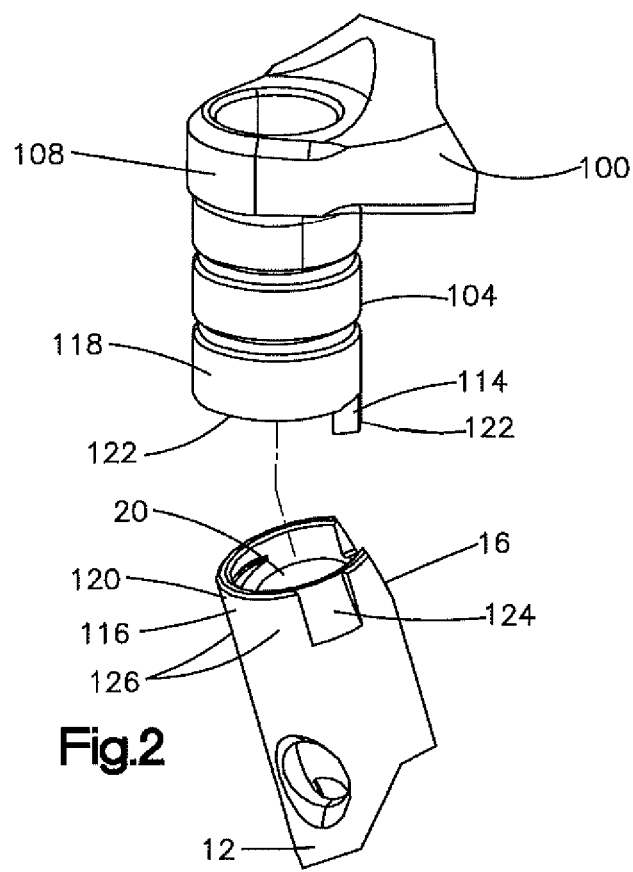

SELF-RETAINING NAIL TO INSERTION HANDLE INTERFACE

BACKGROUND

Fractures are often treated with screws or other fixation devices inserted into or through a bone to stabilize fractured portions thereof once they have been brought into corrective alignment. Fixation treatments for long bones often comprise the insertion of an intramedullary nail into a medullary cavity of the bone. Insertion handles enable the user to insert an intramedullary nail into the medullary canal of a bone through a small incision. However, many insertion handle-to-nail interfaces require one user to hold the insertion handle and nail together while someone else locks the two components using, for example, a connecting screw.

SUMMARY

The present invention relates to an implant insertion assembly comprising an insertion handle extending from a proximal end to a distal end, the distal end including a recessed portion, an outer wall of the recessed portion having a first shape about a perimeter thereof and including an engagement mechanism and an implant extending from a distal end to a proximal end including an opening configured to receive the recessed portion of the insertion handle, the opening having a second shape configured to mechanically interlock with the outer wall of the recessed portion when the recessed portion is inserted therein to transmit torque from the insertion handle to the implant, the proximal end including a receiving structure in a wall thereof, the receiving structure being positioned and oriented to receive the engagement mechanism to removably lock the insertion handle to the implant in the axial direction.

The present invention also relates to an implant insertion assembly for inserting an implant comprising an insertion handle extending from a proximal end to a distal end, the distal end having a shape configured to mate with a proximal end of an implant to which it is to be coupled having a corresponding shape, mechanically interlocking therewith so that, when coupled to an implant, torque is transmitted from the insertion handle to an implant coupled thereto, the distal end including a coupling mechanism configured to engage with the proximal end of an implant to which it is coupled to axially lock the insertion handle to an implant to which it is coupled.

The present invention also relates to an implant insertion assembly comprising an insertion handle extending from a proximal end to a distal free end and including a channel extending therethrough and two opposing cutouts, a distal surface of the insertion handle including two opposing convexly curved portions positioned between the cutouts and an implant extending from proximal end including an opening to a distal end, the distal end including two proximally extending tabs configured to be inserted into the cutouts, a proximal surface of the implant including two opposing concavely curved portions configured to engage the convexly curved portions of the insertion handle.

BRIEF DESCRIPTION

FIG. 1 shows a perspective view of an insertion handle and nail according to an exemplary embodiment of the present disclosure;

FIG. 2 shows a perspective view of an insertion handle-to-nail interface according to a first exemplary embodiment of the present disclosure;

DETAILED DESCRIPTION

Figure 3:
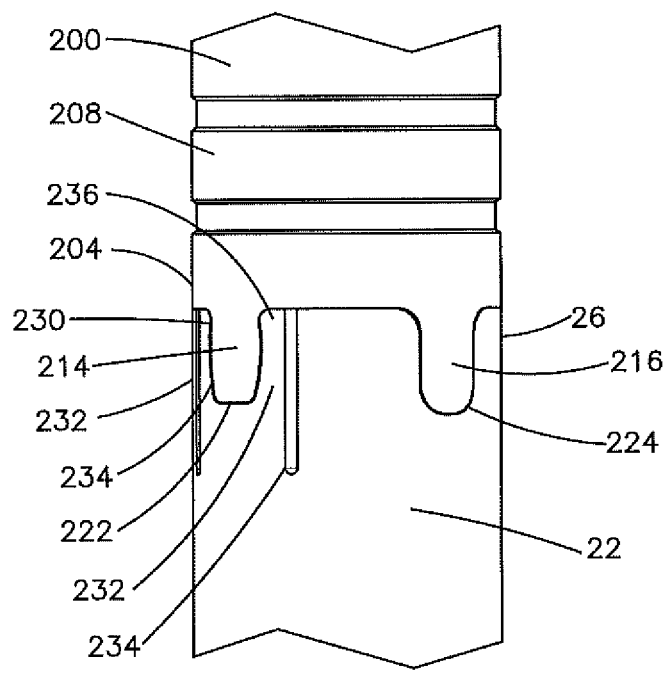
FIG. 3 shows a perspective view of an insertion handle-to-nail interface according to a second exemplary embodiment of the present disclosure.

The present invention may be further understood with reference to the following description and the appended drawings. The present invention relates generally to devices and methods for fixation and stabilization of inter-trochanteric fractures. It is noted that, although embodiments of the present invention have been described with respect to particular bones, the present invention may also be employed in any of a variety of suitable bone fixation procedures including, but not limited to, the fixation of femoral fractures and fractures of other long bones or any other bone in the body. The present invention relates to an insertion handle for inserting an intramedullary nail into a femur. The exemplary insertion handle according to the invention includes a barrel portion, a free end of which engages a proximal end of the intramedullary nail to guide insertion and orientation thereof relative to the bone. Exemplary embodiments describe a free end of the barrel portion that includes an insertion handle-to-nail interface temporarily retaining a position of the intramedullary nail thereagainst prior to the establishment of a more stable connection between the nail and the insertion handle, for example, via insertion of a connection screw into the handle-to-nail interface. In exemplary embodiments, a snap-fit or "quick-click" connection facilitates nail to handle assembly by a single person which self-retaining connection then permits the same person to finalize the more stable connection. However, those skilled in the art will understand that other coupling mechanisms may be employed without departing from the scope of the invention. The interfaces described herein provide precise assembly and alignment between the nail and the insertion handle. It should be noted that the terms "proximal" and "distal" as used herein refer to a direction toward (proximal) and away from (distal) a user of the device such as a surgeon implanting the nail.

As shown in FIGS. 1-2, an insertion handle 100 according to the invention includes a handle portion 101 and a barrel portion 108, the barrel portion 108 extending between a proximal end 103 that is coupled to the handle portion and a distal end 104 configured to be coupled to an intramedullary nail 12. The distal end 104 of the barrel portion 108 includes a channel 112 extending therethrough along an axis which, in an operative position, is substantially aligned with a longitudinal axis of the nail 12 so that a connecting screw 150 inserted therethrough aligns with an opening 20 extending into a proximal end of the intramedullary nail 12. The barrel portion 108 includes a transverse opening 110 angled and dimensioned to receive a tool (not shown) against which a surgeon may hammer to drive a nail 12 connected thereto into the bone, as those skilled in the art will understand.

The distal end 104 of the barrel portion 108 includes a nail interface configured to preliminarily couple the insertion handle 100 to the intramedullary nail 12 via a temporary locking arrangement as the distal end 104 is inserted into the opening 20 in the proximal end of the nail 12. In a first embodiment, shown in FIG. 2, the free end 104 includes a recess 114 configured and dimensioned to engage a tab 116 provided on a proximal end of the intramedullary nail 12. The recess 114 includes a cavity 118 sized and shaped to removably house an increased thickness flange 120 of the tab 116 with a snap-fit engagement. Thus, when the insertion handle 100 is positioned over the intramedullary nail 12 in a desired orientation, the tab 116 snap-fits into the recess 114 preliminarily holding the handle 100 in a desired position and orientation relative to the nail 12 permitting the user to complete the final stable connection between the handle 100 and the nail 12 without requiring assistance from another person. For example, the preliminary connection allows the user to insert and tighten a connecting screw 150 in the channel 112. The distal end 104 of the barrel portion 108 further comprises a substantially hemispherical tab 122 sized and shaped for insertion into a corresponding cutout 124 formed in a proximal end 16 of the intramedullary nail 12. A length of the tab 122 in this embodiment is equal to or smaller than a length of the cutout 124.

Turning now to the intramedullary nail, as shown in FIG. 2, a first wall portion of a proximal end 16 of the intramedullary nail 12 comprises a pair of cutouts 126 defining the tab 116 therebetween. A width of the tab 116 is selected to permit deflection thereof within a predetermined range of motion relative to the intramedullary nail 12 (i.e., to permit deflection thereof into the cavity 142). A second side wall of the proximal end 16 of the intramedullary nail located approximately 90° from the tab 116 includes the substantially hemispherical cutout 124 sized and shaped to receive the hemispherical tab 144. Thus, the nail 12 and the handle 100 may be coupled to one another only when rotated relative to one another in a desired alignment. In an exemplary embodiment, the aiming instrument 100 includes one recess 114 to engage one tab 116. Alternatively, as would be understood by those skilled in the art, any number of additional recesses 114 may be provided to engage a corresponding number of additional tabs 116.

Figure 4:
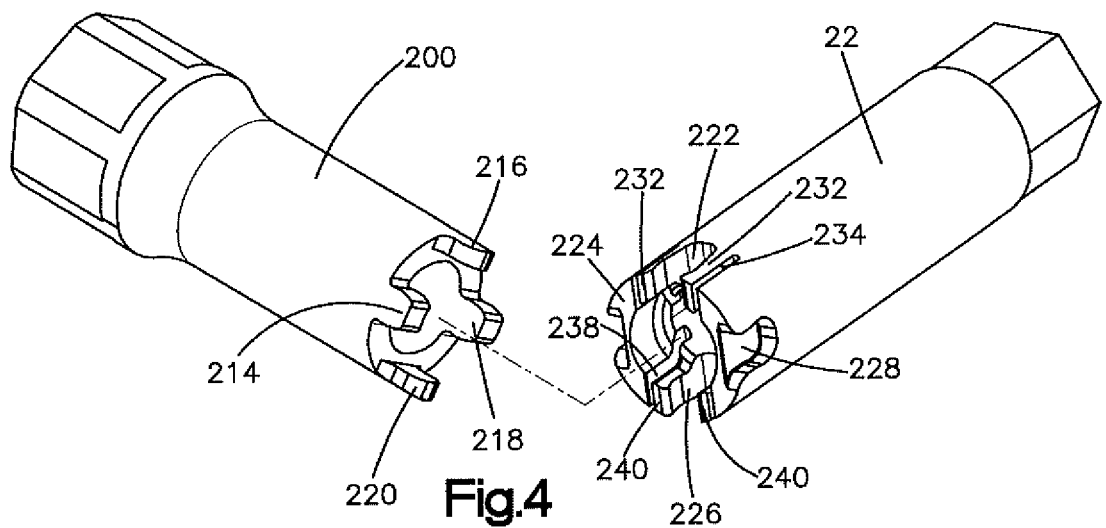
FIG. 4 shows another perspective view of the insertion handle-to-nail interface of the embodiment of FIG. 3.

FIGS. 3-4 show another insertion handle-to-nail interface according to another exemplary embodiment of the present invention. In this embodiment, a distal end 204 of the barrel 208 of the insertion handle 200 includes four rigid tabs 214, 216, 218, 220 extending distally therefrom. The tabs 214, 216, 218, 220 of this embodiment are uniformly distributed around the circumference of the distal end 204 of the insertion handle 200 and each is sized and shaped for insertion into corresponding cutout 222, 224, 226, 228 formed in the proximal end 26 of the intramedullary nail 22. In an exemplary embodiment, the tabs 214, 216, 218, 220 are separated from one another by approximately 90 degrees. Each of the four tabs 214, 216, 218, 220 is substantially hemispherical and has a length equal to or smaller than a length of the corresponding cutout 222, 224, 226, 228. Each of two opposing tabs 214, 218 is formed with an undercut 230 at each side of its base (i.e., at the proximal ends of the tabs 214, 218) on lateral sides thereof. The tabs 214, 218 are configured to fit within two opposing cutouts 222, 226 on the intramedullary nail 22 formed between flexible cantilever beams 232 such that the undercuts 230 removably house a distal end of the cantilever beams 232 with a snap-fit engagement, as discussed in further detail below. Thus, when the insertion handle 200 is positioned over the intramedullary nail 22 in a desired orientation, the distal ends of the cantilever beams 232 snap fit into the undercuts 230 of the tabs 214, 218, eliminating the need for a user to manually hold the intramedullary nail 22 in place while the connecting screw 150 is inserted into the channel 212.

Turning to the proximal end of the intramedullary nail 22, as shown in FIG. 3, a first pair of slots 234 and the substantially hemispherical cutout 222 define a first pair of cantilever beams 232 therebetween. The slots 234 and cutouts 222 extend through the wall of the nail 22 from a radially outer surface to a radially inner surface thereof. A width of each of the beams 232 is selected to permit lateral deflection thereof within a predetermined range of motion when the corresponding tab 214 is inserted into the cutout 222. Proximal ends 236 of the beams 232 are configured to fit within the undercuts 230 of the tab 214. A second pair of slots 238 and the substantially hemispherical cutout 226 define a second pair of cantilever beams 240 located approximately 180 degrees from the first pair of cantilever beams 232. Again, a width of the beams 240 is selected to permit lateral deflection thereof within a predetermined range of motion when the corresponding tab 218 is inserted into the cutout 226. When the tabs 214, 218 are inserted into the cutouts 222 226, the proximal ends of the beams 232, 240 deflect into the undercuts 230, causing an audible clicking noise. This clicking sound serves as audible confirmation of correct assembly between the insertion handle 200 and the nail 22. The proximal end 26 also includes two further substantially hemispherical cutouts 224, 228 disposed approximately 90 degrees between the cutouts 222, 226. As would be understood by those skilled in the art, the cutouts 224, 228 may extend only partially through the wall of the nail 22 or completely therethrough. Thus, the tabs 216, 218 may have a thickness smaller than that of the tabs 214, 218. The tabs 214, 216, 218, 220 and their corresponding cutouts 222, 224, 226, 228 help the user correctly align the insertion handle 200 with the nail 22. Specifically, the nail 22 and the insertion handle 200 may be coupled together only when rotated to a desired alignment (i.e., with each of the tabs 214, 216, 218, 220 aligned with its corresponding cutout 222, 224, 226, 228). In this exemplary embodiment, the intramedullary nail 22 includes four recesses to engage the four tabs of the insertion handle, which enables torque to be easily transmitted from the insertion handle 200 to the nail 22. However, it will be understood that any number of recesses may be provided to engage a corresponding number of tabs.

Figure 5:
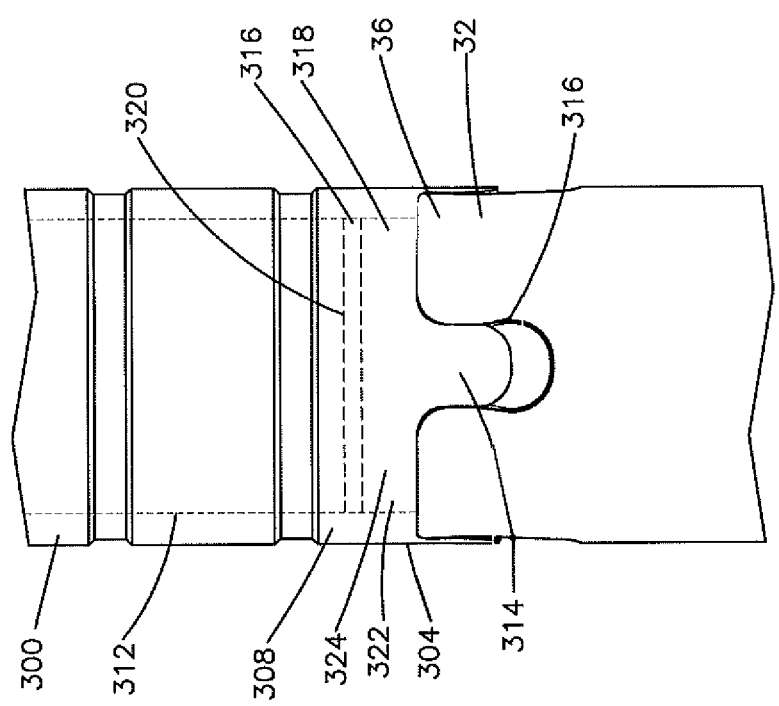
FIG. 5 shows a perspective view of an insertion handle-to-nail interface according to a third exemplary embodiment of the present disclosure.

An insertion handle-to-nail interface according to another exemplary embodiment is shown in FIG. 5. Specifically, the free end 304 of a barrel 308 of an insertion handle 300 includes a tab 314 extending distally therefrom sized and shaped for insertion into a corresponding cutout 316 formed in a proximal end 36 of the intramedullary nail 32. A length of the tab 314 in this embodiment is equal to or smaller than the length of the cutout 316. In an exemplary embodiment, the insertion handle 300 may include two opposing tabs 314 separated from one another by approximately 180 degrees. The tabs 314 allow for easy rotational alignment of the insertion handle 300 and the intramedullary nail 32 by the user. The insertion handle 300, in this embodiment, also includes an internal ridge 316 extending circumferentially about an inner surface of the opening 308. The ridge 316 may be, for example, a raised band on the inner surface extending about the circumference of the channel 312. The ridge 316 is configured and dimensioned to engage a circumferential recessed portion 318 on the proximal end of the intramedullary nail 32. For example, the ridge 316 is sized and shaped to fit within a groove 320 extending about the circumference of the recessed portion 318, creating a snap-fit or quick-click engagement. Thus, when the insertion handle 300 is positioned over the intramedullary nail 32 in a desired orientation, the ridge 316 snap-fits into the groove 320 eliminating the need for a user to manually hold the intramedullary nail 32 in place while the connecting screw 150 is inserted into the channel 312.

Turning to the intramedullary nail 32, as shown in FIG. 5, the proximal end 36 includes a recessed portion 318, described above, which extends about the circumference of the proximal end 36. The recessed portion 318 is configured and dimensioned to fit within the channel 312 and engage the inner surface thereof. More specifically, as described above, a groove 320 extending along the recessed portion 318 is sized to engage the ridge 316 provided on the inner surface. In an exemplary embodiment, rather than the recessed portion 318 extending about the entire circumference of the nail 32, the proximal end 36 may include a plurality of slots 322 defining separate recessed tabs 324 therebetween. Each of the tabs 324 of this exemplary embodiment also includes a groove 320 configured to engage the ridge 316. The tabs 324, in this embodiment, allow for deflection thereof within a predetermined range of motion relative to the insertion handle 300 (i.e., to permit deflection thereof into the channel 312 to receive the ridge 316 within the groove 320. When the groove 320 engages with the ridge 316 of the insertion handle 300, an audible clicking noise is audible serving as confirmation of correct assembly between the insertion handle 300 and the nail 32.

Figure 6:
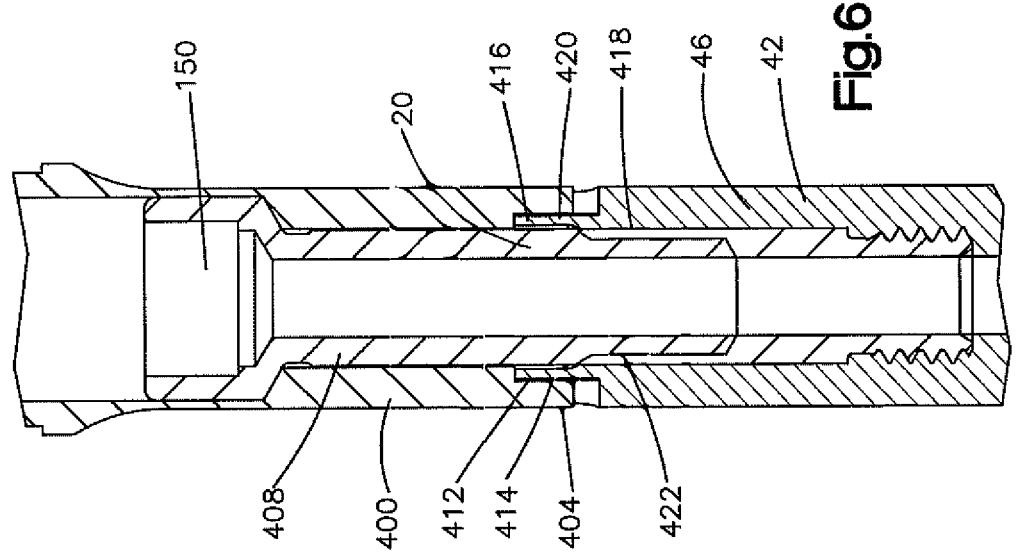
FIG. 6 shows a perspective view of an insertion handle-to-nail interface according to a fourth exemplary embodiment of the present disclosure.

FIG. 6 depicts an insertion handle-to-nail interface according to yet another embodiment of the invention. In this embodiment, the free end 404 of the barrel 408 of an insertion handle 400 includes a groove 414 extending about a circumference of an inner surface of the channel 412 and configured to engage a flange 416 on the proximal end 46 of a nail 42. In another exemplary embodiment, the insertion handle 400 includes an increased thickness ridge instead of a groove extending about the circumference of the channel 412 and configured to engage the flange 416 when it is inserted distally therepast.

The intramedullary nail 42 of this embodiment includes a flexible recessed portion 418 extending proximally past a proximal end 46 of the nail 42. The flexible recessed portion 418 extends about the entire circumference of the proximal end 46 of the nail and has a thickness that allows the recessed portion 418 to deflect radially inwardly toward a center axis, L, of the nail 42 and outwardly away from a center axis of the nail 42. Thus, a thickness of the wall 420 of the recessed portion 418 is sufficiently thin to permit it to flex without plastic deformation. The recessed portion 418 includes an increased diameter flange 416, as described above, disposed about a proximal tip. The flange 416 may extend about the entire circumference of the outer surface of the recessed portion 418 or may only be positioned on lateral sides thereof. The flange 416 is configured to be removably housed within the groove 414 via a snap-fit engagement, creating an audible clicking sound signaling to the user that the intramedullary nail 42 and insertion handle 400 are axially locked to one another. An inner surface 422 of the recessed portion 418 is milled to a substantially conical shape. Specifically, a diameter of the opening 20 at the proximal end of recessed portion 418 is larger than a diameter of the opening 20 at a distal end of the recessed portion 418, as can be seen in the figure. Thus, once the flange 416 is snap-fit into the groove 414, the screw 150 may be inserted through the channel 412 into the conical portion of the opening 20 such that an outer surface of the screw 150 pushes the flange 416 outward circumferentially, securing the connection between the nail 42 and the insertion handle 400 for further clinical steps.

Figure 7:
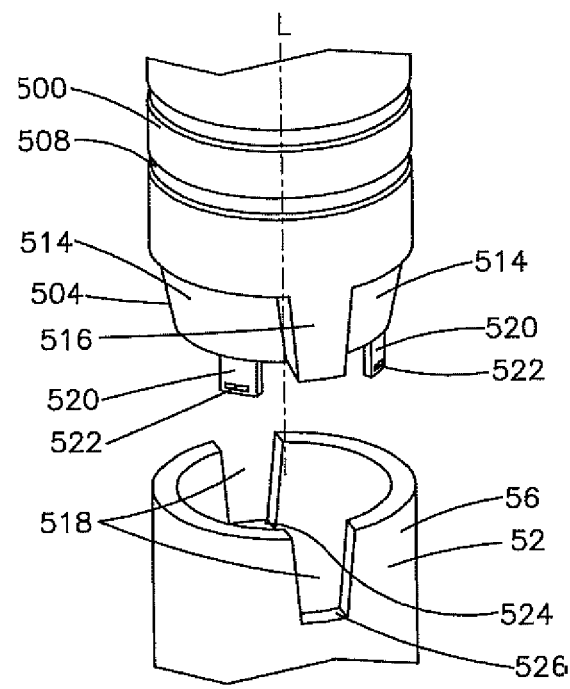
FIG. 7 shows a perspective view of an insertion handle-to-nail interface according to a fifth exemplary embodiment of the present disclosure.

FIG. 7 depicts an insertion handle-to-nail interface according to yet another embodiment of the invention. In this embodiment, the free end 504 of the barrel 508 of an insertion handle 500 includes a spring-locking mechanism. Specifically, the free end 504 of the insertion handle 500 includes two recessed portions 514 configured to engage an inner surface of the proximal end 56 of the intramedullary nail 52. Positioned between the two recessed portions 514 are two non-recessed portions 516 configured to engage two cutouts 518 in the outer surface of the intramedullary nail 52. The non-recessed portions 516 taper distally so that they are substantially trapezoidal in shape, as can be seen in the figure, and have a width that is equal to or slightly smaller than the width of the cutouts 518. The non-recessed portions 516 allow the user to easily rotationally align the insertion handle 500 with the intramedullary nail 52 as well as provide torque and rotation transmission from the insertion handle 500 to the nail 52 when the two components are coupled together. The insertion handle 500 may further include a plurality of tabs 520 extending distally from the recessed portions 514. In an exemplary embodiment, there are four flexible tabs 520 distributed evenly around the circumference of the free end 504. However, it will be understood that any number of tabs may be used. Each of the tabs 520 includes an increased thickness ridge 522 extending radially outward along the width of the tab 520 and sized and shaped to removably engage a circumferential ridge 524 on in the inner surface of the intramedullary nail 52 with a snap-fit or quick click engagement. A width of each of the tabs 520 is selected to permit radial deflection thereof within a predetermined range of motion (i.e., to permit deflection thereof when passing the ridge 524 of the nail 52).

The intramedullary nail 52 of this embodiment, as described above, comprises a pair of cutouts 518 extending from an outer surface of the intramedullary nail 52 to an inner surface thereof. The cutouts 518 taper distally to a distal wall 526, defining a substantially trapezoidal shape corresponding to the trapezoidal non-recessed portions 516. The intramedullary nail 52 also includes a rounded ridge 524 extending about the circumference of an inner surface of the proximal end 56. The ridge 524 is configured to engage a proximal surface of the ridge 522 on the tabs 520. That is, when the insertion handle 500 is inserted into the intramedullary nail 52, the ridge 524 causes the tabs 520 on the insertion handle 500 to deform towards the center axis of the insertion handle 500. As the insertion handle 500 is pushed further distally into the nail 52 and the ridge 522 moves distally past the ridge 524 on the nail 52 and the tabs 520 snap back outwardly, in a direction away from a central, longitudinal axis L of the insertion handle 500, creating an audible clicking sound. Thus, the engagement of the two ridges 522, 524 holds the insertion handle 500 and nail 52 in a temporary locking arrangement. In another exemplary embodiment, instead of a ridge, the nail 52 may have a groove extending about a circumference of the inner surface thereof configured to removably house the ridge 522 of the insertion handle 500 therein with a snap-fit engagement.

Figure 8:
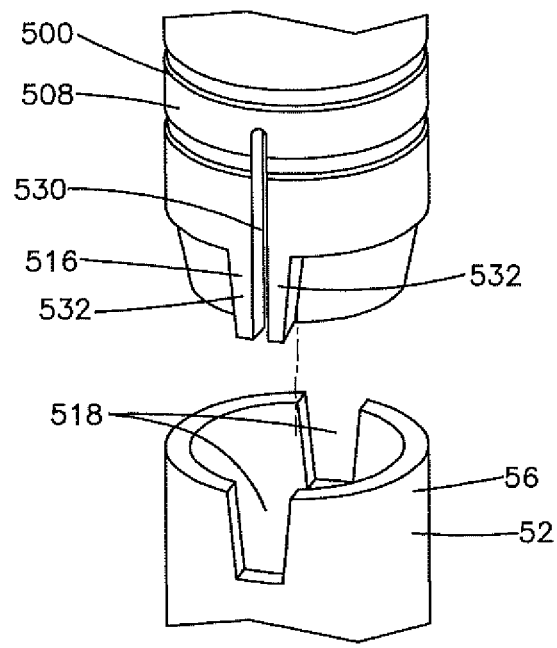
FIG. 8 shows a perspective view of an insertion handle-to-nail interface according to a sixth exemplary embodiment of the present disclosure.

In an exemplary embodiment, depicted in FIG. 8, in lieu of tabs, the non-recessed portions 516 are configured for a friction-fit interface between the insertion handle 500 and the nail 52. Specifically, the insertion handle 500 includes a slot 530 extending longitudinally through each of the non-recessed portions 516 from an outer surface of the insertion handle 500 to an inner surface thereof, defining two flexible members 532. The flexible members 532 are deflectable laterally within a predetermined range of motion—i.e., the flexible members 532 are deflected toward one another into the slot 530 when inserted into the cutouts 518. In this embodiment, the width of the non-recessed portions 516, including the slots 530, is larger than the width of the cutouts 518 in the nail 52. Thus, the cutouts 518 force the flexible members 532, which are biased toward a separated position, to flex toward one another when inserted therein, so that the flexible members 532 project an outward lateral force against the side walls of the cutouts 518, holding the insertion handle 500 and the nail 52 together via friction fit.

Figure 9:
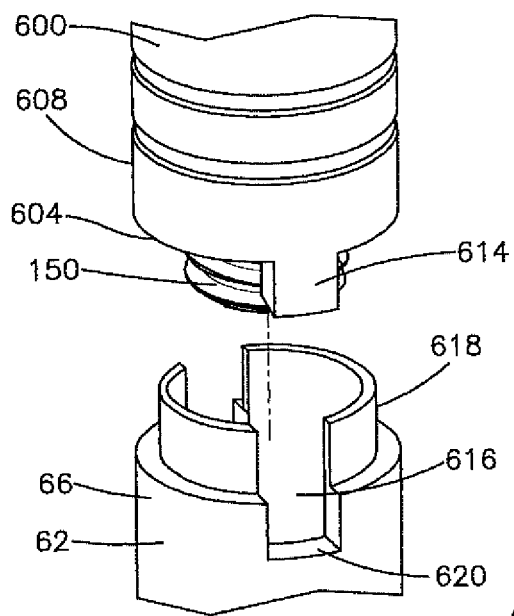
FIG. 9 shows a perspective view of an insertion handle-to-nail interface according to a seventh exemplary embodiment of the present disclosure.
Figure 10:
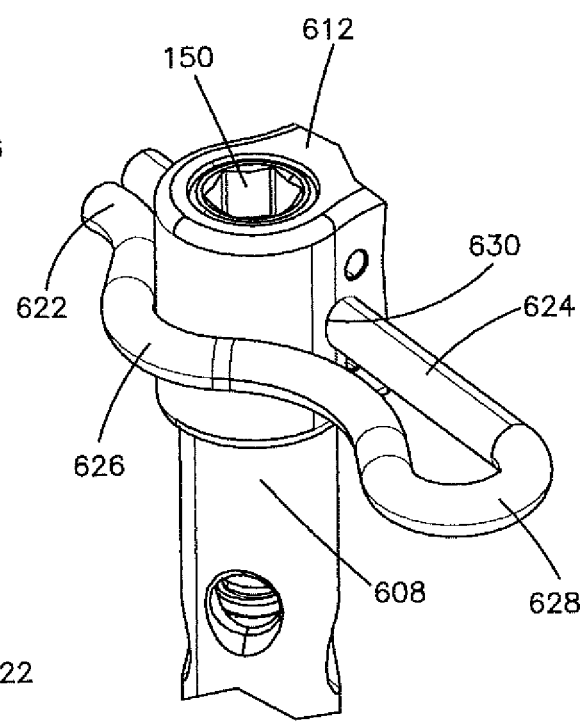
FIG. 10 shows a top perspective view of the barrel of the insertion handle of FIG. 9.
Figure 11:
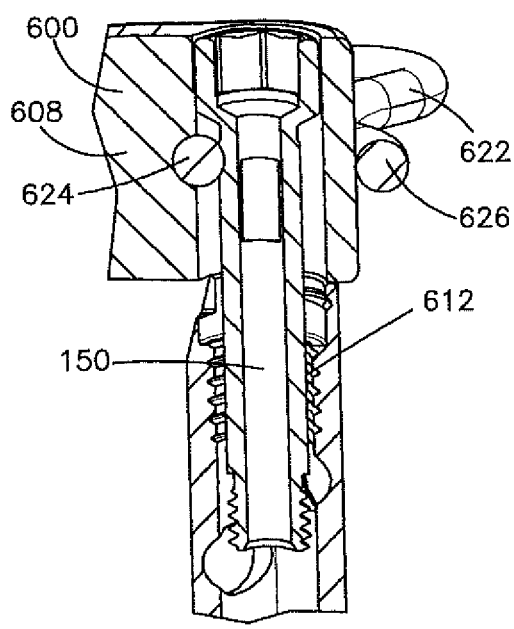
FIG. 11 shows a cross-sectional view of the barrel of the insertion handle of FIG. 9.

FIGS. 9-11 depict a friction fit insertion handle-to-nail interface according to another exemplary embodiment of the invention. In this embodiment, the distal end 604 of the barrel 608 of the insertion handle 600 includes two opposing rigid tabs 614 extending distally therefrom. The tabs 614 are separated by approximately 180 degrees and are sized and shaped for insertion into two corresponding cutouts 616 formed in the proximal end 66 of the nail 62. The tabs 614 taper distally so that they are substantially trapezoidal in shape, as can be seen in the figure, and have a width that is equal to or slightly larger than the width of the cutouts 616 so as to hold the insertion handle 600 and the nail 62 together by friction fit. The tabs 614 allow the user to easily rotationally align the insertion handle 600 with the intramedullary nail 62 as well as provide torque and rotation transmission from the insertion handle 600 to the nail 62 when the two components are coupled together.

The intramedullary nail 62 of this embodiment, comprises a pair of recessed portions 618 separated by the cutouts 616. The recessed portions 618 are configured to fit within the channel 612 of the insertion handle 600. The cutouts 616 extend from an outer surface of the intramedullary nail 62 to an inner surface thereof. The cutouts 616 taper distally to a distal wall 620, defining a substantially trapezoidal shape corresponding to the trapezoidal tabs 614. Thus, insertion of the tabs 614 into the cutouts 616 rotationally lock the insertion handle 600 and nail 62. In this embodiment, the screw 150, when inserted through the channel 612 and threadedly screwed into the nail 62, axially fixes the insertion handle 600 to the nail 62. This tightening of the screw 150 into the nail 62 also further presses the tabs 614 into the cutouts 616. The interface of this embodiment further includes a clip 622 which keeps the screw 150 in place when assembling the connection between the nail 62 and the handle 600. The clip 622 includes two arms 624, 626, connected together by a rounded connection portion 628 to substantially form a U-shape. The first arm 624 is straight and sized and shaped to be inserted through a transverse hole 628 open to the barrel 608. The second arm 626 includes a rounded portion configured to conform to the shape of a lateral outer surface of the barrel 608. The clip 622 is biased to pinch closed pressing the screw 150 against an interior surface of the channel 612 generating friction that maintains the screw 150 in place while the handle and nail are coupled to one another.

Figure 12:
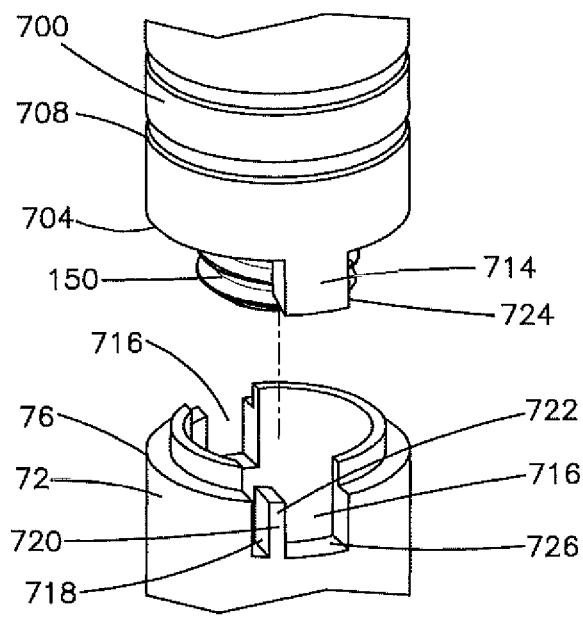
FIG. 12 shows a perspective view of an insertion handle-to-nail interface according to an eighth exemplary embodiment of the present disclosure.

FIG. 12 depicts a friction fit insertion handle-to-nail interface according to yet another exemplary embodiment of the invention. In this embodiment, the distal end 704 of the barrel 708 of the insertion handle 700 includes two opposing rigid tabs 714 extending distally therefrom. The tabs 714 are separated by approximately 180 degrees and are sized and shaped for insertion into corresponding cutouts 716 formed in the proximal end 76 of the nail 72. Each of the tabs 714 is substantially rectangular and has a length equal to or smaller than a length of the cutout 716.

The intramedullary nail 72 of this embodiment, as described above, includes two substantially rectangular cutouts 716 substantially corresponding to the shape of the tabs 714. The nail 72 also includes two slots 718, each positioned adjacent to the cutouts 716 to define two flexible cantilever beams 720. A width of each of the beams 720 is selected to permit lateral deflection thereof within a predetermined range of motion when the corresponding tab 714 is inserted into the cutout 716. A width of each of the cutouts 716 is slightly smaller than a width of each of the tabs 714 so that the insertion handle 700 and the nail 72 are held together via friction. The tabs 714 and their corresponding cutouts 716 help the user correctly align the insertion handle 700 with the nail 72. Specifically, the nail 72 and the insertion handle 700 may be coupled only when rotated to a desired alignment (i.e., with each of the tabs 714 aligned with a corresponding one of the cutouts 716). In this exemplary embodiment, the intramedullary nail 72 includes two cutouts 716, each engaging a corresponding one of the two tabs 714 of the insertion handle 700, which enables torque to be easily transmitted from the insertion handle 700 to the nail 72. As would be understood by those skilled in the art, any number of cutouts may be provided to engage a corresponding number of tabs. In an exemplary embodiment, proximal ends 722 of the beams 720 may also include an engagement mechanism 724 such as, for example, a ridge or a groove on a lateral surface facing the cutouts 716 configured to engage with a corresponding engagement mechanism 726 (i.e., a ridge or groove) on the lateral opposing surface of the tabs 714. As those skilled in the art will understand, any of the various arrangements of mating pairs of tabs and cutouts may be mixed and matched as desired or the dimensions of the various tabs and cutouts may be varied so that the nail and the handle will mate in only a single desired rotational alignment. When the tabs 714 are inserted into the cutouts 716 the proximal ends 722 of the beams 720 deflect into the engagement mechanism 726 on the cutouts 716.

Figure 13:
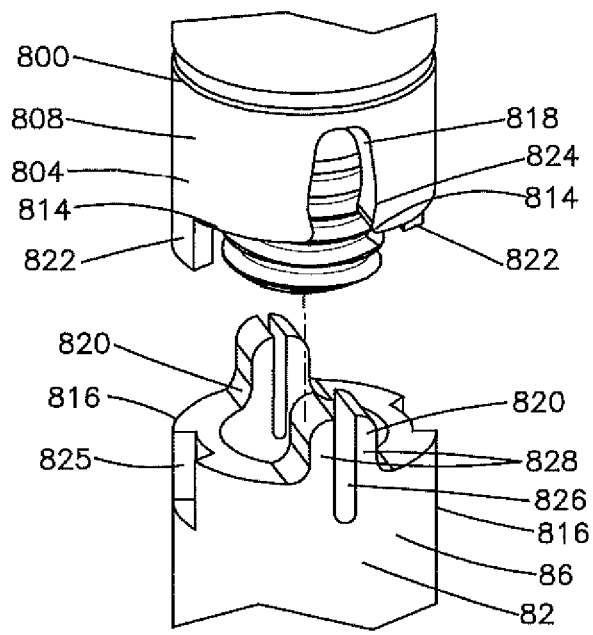
FIG. 13 shows a perspective view of an insertion handle-to-nail interface according to a ninth exemplary embodiment of the present disclosure.

FIG. 13 depicts an insertion handle-to-nail snap interface according to yet another exemplary embodiment of the invention. In this embodiment, the distal free end 804 of the barrel 808 of an insertion handle 800 and the proximal end 86 of the nail 82 have matching profiles. Specifically, the distal end 804 of the insertion handle 800 includes two opposing convexly rounded portions 814 while the proximal end 86 of the nail 82 has two opposing concavely rounded portions 816 configured to fit with the convex portions 814. Both the convex portions 814 and the concave portions 816, in this embodiment, are substantially hemispherical. However, it will be understood that the profiles of the distal end 804 of the insertion handle 800 and the proximal end 86 of the nail 82 may have any geometry so long as they are configured to fit together. These mating profiles allow the user to easily rotationally align the insertion handle 800 and the nail 82 in the correct positions while also aiding in transmitting torque from the handle 800 to the nail 82. Looking to the insertion handle 800, the distal end 804 further includes two rounded opposing cutouts 818 positioned between the convex portions 814 and extending from an outer surface of the insertion handle 800 to an inner surface thereof. The cutouts 818 in this embodiment are substantially circular and open to the distal end 804. The cutouts 818 are configured and dimensioned to receive tabs 820 provided on a proximal end of the nail 82. A neck portion 824 of the cutouts 818 has a width smaller than a diameter of the tabs, providing a temporary snap-connection, as described in further detail below. The insertion handle 800 further includes two distally-extending tabs 822 positioned at the distal-most point of the convex portions 814. Thus, the tabs 822 are separated from the cutouts 818 by approximately 90 degrees. The tabs 822 may be, in this embodiment, substantially rectangular and are sized and shaped for insertion in two corresponding cutouts 825.

The intramedullary nail 82 of this embodiment includes two substantially circular tabs 820 extending from a proximal end thereof. Each of the tabs 820 includes a longitudinally extending slot 826 open to the proximal end of the tabs 820 which bisects the tab 820 into two flexible members 828. Each of the tabs 820 has a diameter larger than that of the neck portion 824 of the corresponding cutouts 818 and is configured to be removably housed within the cutout 818 with a snap-fit engagement. Thus, when the insertion handle 800 is positioned over the intramedullary nail 82 in a desired orientation, the tabs 820 snap fit into the cutouts 818. Specifically, the flexible members 828, when they come into contact with the neck portion 824, deflect radially inward to pass through the neck portion 824. When the flexible members 828 pass through the neck portion 824, they snap away from each other, temporarily locking the tabs 820 within the cutouts 818 with an audible clicking noise. The distal end 804 of the nail 82 further comprises two cutouts 825 extending from an outer surface at least partially through the wall of the nail 82. The cutouts 825 are sized and dimensioned to engage the tabs 822 and have a substantially rectangular profile. Thus, the nail 82 and the insertion handle 800 may be coupled only when rotated to a desired alignment. The tabs 824, when inserted into the cutouts 825, provide increased torque transmission from the insertion handle 800 to the nail 82.

Figure 14:
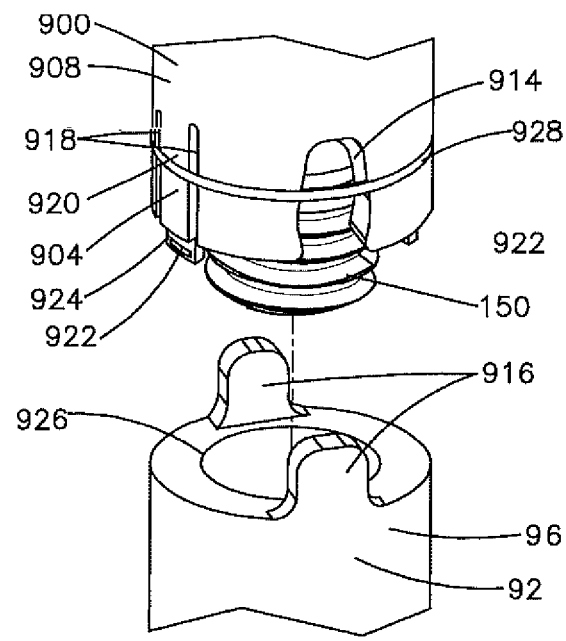
FIG. 14 shows a perspective view of an insertion handle-to-nail interface according to a tenth exemplary embodiment of the present disclosure.

FIG. 14 depicts an insertion handle-to-nail snap interface according to yet another exemplary embodiment of the invention. In this embodiment, a distal free end 904 of the barrel 908 of an insertion handle 900 includes two opposing rounded cutouts 914 configured and dimensioned to engage two opposing tabs 916 provided on a proximal end 96 of an intramedullary nail 92. In the insertion handle 900 of FIG. 14, the cutouts 914 are shown to be substantially circular, similar to the cutouts 818. However, it will be understood that the cutouts 914 may be any shape, so long as the profiles fit with the profiles of the tabs 916. The insertion handle 900 further includes a pair of parallel slots 918 extending longitudinally along the distal end 904 of the handle 92 and defining a flexible beam 920 therebetween. The slots 918 extend from the outer surface of the insertion handle 900 to an inner surface thereof. A length of each of the slots 918 may be chosen depending on the desired range of deflection of the beam 920. For example as would be understood by those skilled in the art, longer slots 918 provide the beam 920 with a greater range of deflection while shorter slots 918 provide the beam 920 with a smaller range of deflection. In an exemplary embodiment, the slots 918 may be, for example, approximately 16-18 mm. In an exemplary embodiment, the insertion handle 900 includes two pairs of slots 918 defining a pair of opposing beams 920. In this embodiment, the beams 920 may be separated by approximately 180 degrees. The beams 920 each include a tab 922 extending from a distal end thereof and configured to engage an inner surface of the nail 92 with a snap-fit engagement. For example, each of the tabs 922 may include a mating feature 924 such as a groove or an undercut extending across the width of each of the tabs 922. Each of the mating features 924, in this embodiment, is sized and shaped to engage a corresponding mating feature 926 on a radially inner surface of the nail 92 via a snap-fit or quick-click engagement. In an exemplary embodiment, the insertion handle 900 further includes a supporting ring 928 extending about at least a portion of the circumference of the distal end 904, as shown in FIG. 14. The supporting ring 928 provides further support to the beams 920 and the distal end 904 of the handle 900 when the handle 900 is coupled to the nail 92.

A proximal end 96 of the intramedullary nail 92 of this embodiment includes the two tabs 916 extending proximally therefrom each of which is configured to fit within a corresponding one of the cutouts 914. The tabs 916 shown in FIG. 14 are substantially rectangular. However, it will be understood that the tabs 916 may take any shape so long as they fit within the cutouts 914 of the insertion handle 900. As with previous embodiments, the tabs 916 and the cutouts 914 allow the user to easily align the insertion handle 900 with the nail 92 in the correct orientation while also provide increased torque and rotation transmission from the insertion handle 900 to the nail 92. The nail 92 further includes the circumferential mating feature 926 along the inner surface thereof. The mating feature 926 in this embodiment is a circumferential increased thickness ridge that engages the mating feature 924 on the tabs 922 of the insertion handle 900. For example, when the insertion handle 900 is inserted into the proximal end of the nail 92, the beams 920 with the tabs 922 may deflect inwardly (toward the central axis of the insertion handle) when the tabs 922 contact an increased thickness portion of the interior surface of the nail 92—i.e., a ridge. However, because the tabs 922 include a mating feature such as a groove or an undercut, as the insertion handle 900 is moved further distally into the nail 92, the ridge will fit within the groove and the tabs 922 will snap back outwardly (away from the central axis of the insertion handle), temporarily locking the two components together and creating an audible clicking noise. This allows the user to know that the insertion handle 900 and the nail 92 are axially coupled correctly. In this embodiment, the screw 150 may provide further support to the connection when inserted into the channel 912. Specifically, the outer surface of the screw 150 exerts a radially outwardly directed force on the interior of the insertion handle 900, pressing the beams 920 and the tabs 922 into the inner surface of the nail 92 and preventing the mating features 924 of the insertion handle 900 from deflecting out of or away from the mating features 926 of the nail 92.

Figure 15:
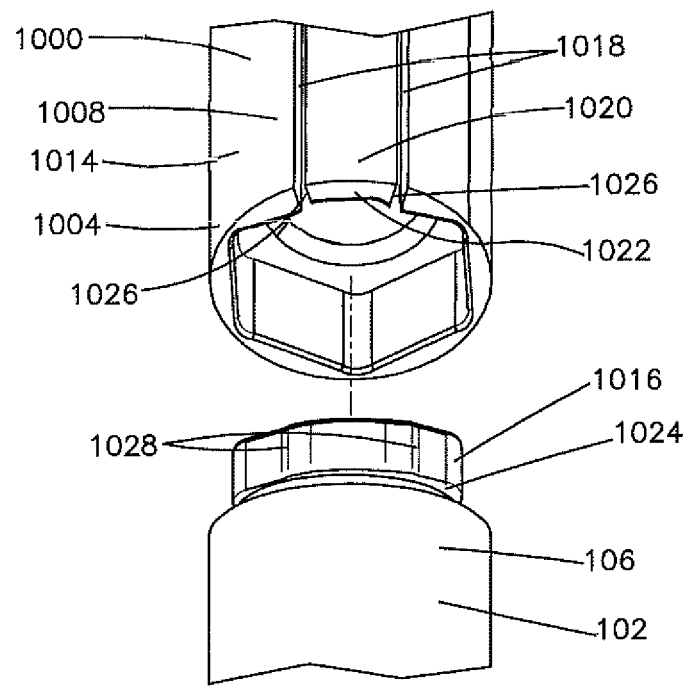
FIG. 15 shows a perspective view of an insertion handle-to-nail interface according to a eleventh exemplary embodiment of the present disclosure.

FIG. 15 depicts an insertion handle-to-nail snap interface according to yet another exemplary embodiment of the invention. In this embodiment, the interior geometry of an insertion handle 1000 is configured to match the exterior geometry of the nail 102. Specifically, in this embodiment, a distal portion 1014 the inner surface of the insertion handle 100 is cut to define a substantially hexagonal shape, as seen in FIG. 15. Similarly, a proximal recessed portion 1016 of the outer surface of the nail 102 is cut to define a substantially hexagonal shape. Thus, the matching hexagonal geometries on the nail 102 and the insertion handle 1000 facilitate easier insertion by the user in a correct orientation, as well as increased torque transmission from the insertion handle 1000 to the nail 102. Turning to the insertion handle 1000, the distal end 1004 of the barrel 1008 according to this embodiment also includes two substantially parallel longitudinal slots 1018 extending from an outer surface of the handle 1000 to an inner surface thereof and defining a flexible beam 1020 therebetween, similar to beams 920 of insertion handle 900. A length of the slots 1018 may be chosen depending on the desired range of deflection of the beam 1020. As indicated above, longer slots 1018 provide the beam 1020 with a greater range of deflection while shorter slots 1018 provide the beam 1020 with a smaller range of deflection. In an exemplary embodiment, the slots 1018 may be, for example, approximately 16-18 mm. The beam 1020 deflects radially inwardly/outwardly when the distal end 1004 comes into contact with the proximal end of the nail 102. The beam 1020, in this embodiment, further includes an increased thickness ridge 1022 extending across the width of the beam 1020 at a distal end thereof. The ridge 1022 is dimensioned to be removably housed within a recess 1024 on the nail 102 with a snap-fit engagement. In an embodiment, the beam 1020 may further include longitudinal ridges 1026 positioned at the lateral portions of the inner surface thereof. The ridges 1026 are configured to fit within longitudinal grooves 1028 on one of the faces of the hexagonal outer surface of the nail 102. The beam 1020 is centrally positioned on one of the sides of the hexagonal profile of the insertion handle 1000 while the grooves 1028 are positioned on a corresponding side of the hexagonal profile of the nail 102. Thus, one face 1030 of the hexagonal geometries of both the handle 1000 and the nail 102 differs from the rest, creating an asymmetrical geometry therein that prevents the user from inserting the nail 102 within the insertion handle 1000 in an incorrect orientation. Therefore, the nail 102 and the insertion handle 1000 may be coupled only when rotated to a desired alignment.

The nail 102 of the present embodiment, as described above, has a proximal recessed portion 1016 with a hexagonal geometry and a circumferential groove 1024 disposed distally of the proximal recessed portion 1016. The grooved portion 1024 of the nail 102 is substantially cylindrical with a diameter smaller than a diameter of the remainder of the nail 102, including the proximal portion 1032. The groove 1024 is sized and shaped to removably house the ridge 1022 on the distal end of the beam 1020 with a snap-fit engagement, creating an audible clicking sound indicating to the user that the insertion handle 1000 and the nail 102 are correctly aligned axially and locked together.

Figure 16:
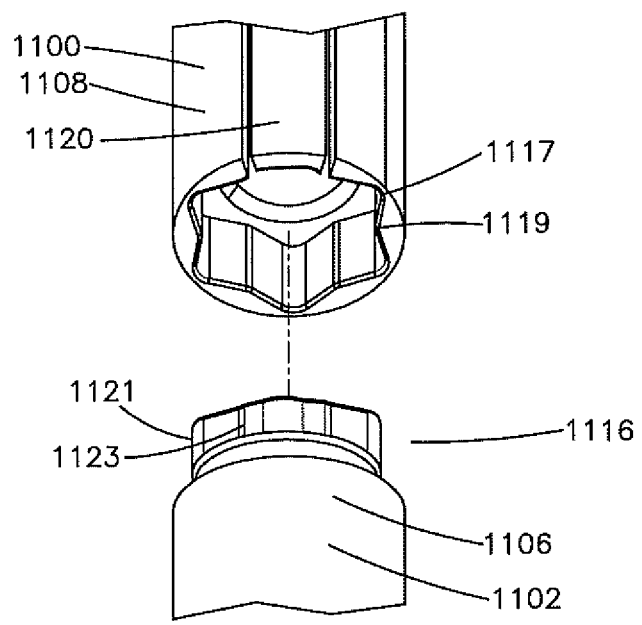
FIG. 16 shows a perspective view of an insertion handle-to-nail interface according to a twelfth exemplary embodiment of the present disclosure.

In another exemplary embodiment shown in FIG. 16, an insertion handle 1100 and a nail 1102 have substantially the same structure as the insertion handle 1000 and nail 102. However, in this embodiment, the internal geometry of the insertion handle 1100, as well as the external geometry of the nail 1102 are substantially hexalobular. Specifically, the internal surface of the insertion handle 1100 and the external surface of the nail 110 are cut into a six-point star-shaped pattern with a plurality of grooves 1117 and protrusions 1119. The insertion handle 1100 includes a set of six substantially similar grooves 1117 and six substantially similar protrusions 1119 which alternate about the inner circumference of the channel 1112. Each groove 1117 corresponds to a "point" on the star-like hexalobular geometry while each protrusion 1119 corresponds to an indentation between each point. In the embodiment of FIG. 16, the beam 1120 of the insertion handle is positioned at one of the "points" so that that point is flatter, or less rounded, than the remaining five points. Similarly, a recessed portion 1116 of the nail 1102 includes a set of six substantially similar protrusions 1121 and six substantially similar grooves 1123 which alternate about the outer circumference of the nail 1102. Each protrusion 1121 corresponds to an indent on the star-like hexalobular geometry while each protrusion 1223 corresponds to a point. However, one of the protrusions of the nail may be substantially flat to enable engagement of the proximal recessed portion 1116 with the beam 1120. In an exemplary embodiment, the grooves 1117, 1123 and protrusions 1119, 1121 of the hexalobular shapes each have a large radius of curvature supporting nail and handle strength as well as reducing manufacturing costs.

Figure 17:
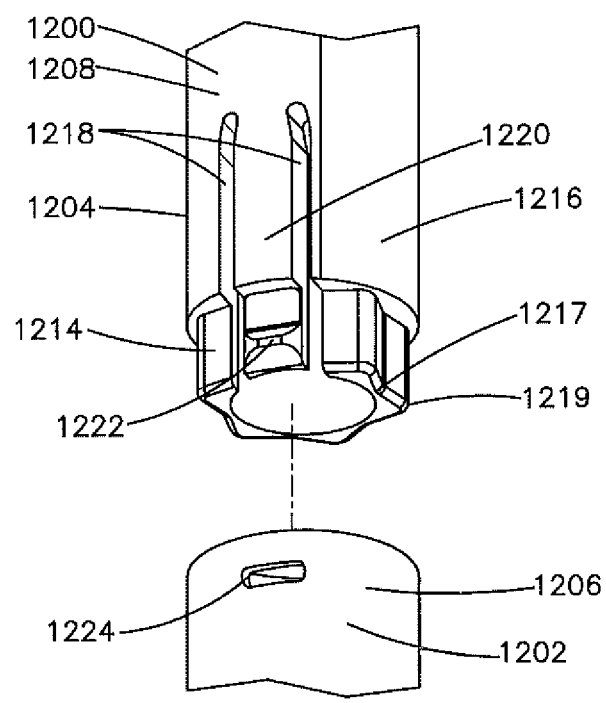
FIG. 17 shows a perspective view of an insertion handle-to-nail interface according to a thirteenth exemplary embodiment of the present disclosure.
Figure 18:
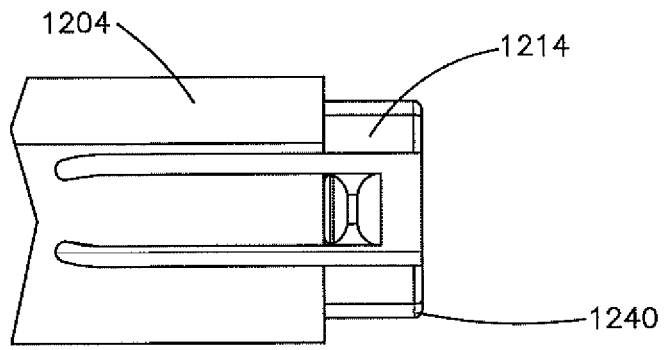
FIG. 18 shows a side view of the distal end of the insertion handle of FIG. 17.
Figure 19:
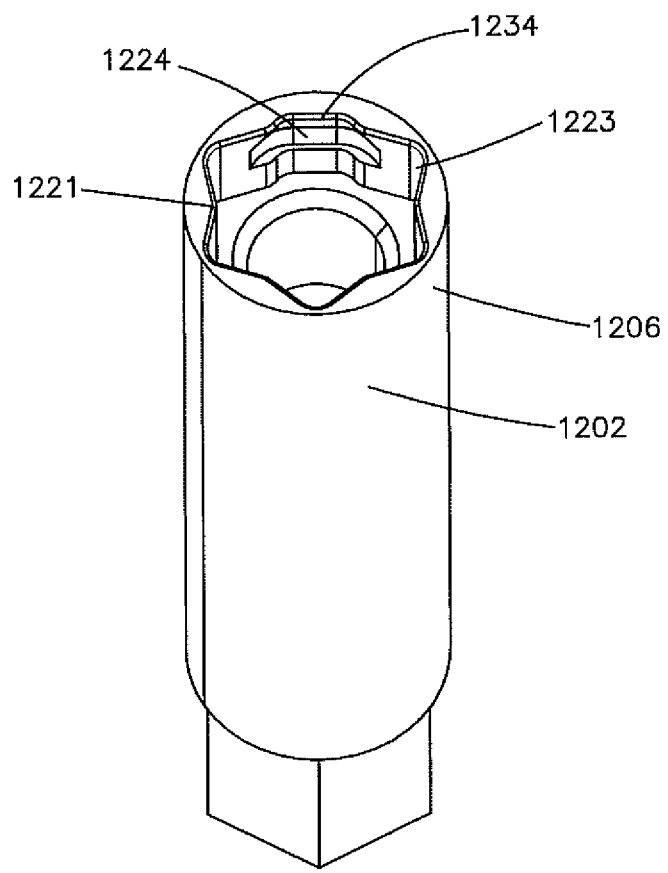
FIG. 19 shows a top perspective view of the nail of FIG. 17.

FIGS. 17-19 depict an insertion handle-to-nail snap interface according to yet another exemplary embodiment of the invention. In this embodiment, the insertion handle 1200 and the nail 1202 also include matching hexalobular geometries, similar to the insertion handle 1100 and nail 1102. However, in this embodiment the insertion handle 1200 is structured to be inserted into the proximal end of the nail 1202. Specifically, the distal end 1204 of the barrel 1208 of the insertion handle 1200 includes a recessed portion 1214 configured and dimensioned to be inserted into and engage an inner surface of the proximal end of the nail 1202. As can be seen in the figures, the recessed portion 1214 defines a hexalobular shape including six "points" extending radially outward. Specifically, the external surface of the recessed portion 1214 and the internal surface of the nail 1202 are cut into a six-point star-shaped pattern with a plurality of grooves 1217 and protrusions 1219. The insertion handle 1200 includes a set of six substantially similar grooves 1217 and six substantially similar protrusions 1219 which alternate about the inner circumference of the channel 1212. Each protrusion 1219 corresponds to a "point" on the star-like hexalobular geometry while each groove 1217 corresponds to an indent between each point. Similarly, the internal surface of the nail 1202 includes a set of six substantially similar protrusions 1221 and six substantially similar grooves 1223 which alternate about the inner circumference of the nail 1102. Each groove 1223 corresponds to a "point" on the star-like hexalobular geometry while each protrusion 1221 corresponds to an indent between each point. In this embodiment, five of the points may be rounded while the sixth point, where a flexible beam 1220 is positioned, has a different geometry to promote insertion of the handle 1200 into the nail 1202 in a correct orientation, as will be described in further detail below. In an exemplary embodiment, the grooves 1217, 1223 and protrusions 1219, 1221 of the hexalobular shapes are enlarged (i.e. the angle between two lobes is large), supporting nail and handle strength as well as reducing manufacturing costs. The insertion handle 1200 may also include two parallel longitudinal slots 1218 extending from an outer surface of the handle 1200 to an inner surface thereof and defining a flexible beam 1220 therebetween, similar to beams 920, 1020. As can be seen in the figure, the slots extend proximally from the distal end of the insertion handle 1200, through the recessed portion 1214 and into a non-recessed portion 1216 of the insertion handle 1200. A length of the slots 1218 may be chosen depending on the desired range of deflection of the beam 1220. For example, longer slots 1218 provide the beam 1220 with a greater range of deflection while shorter slots 1218 provide the beam 1220 with a smaller range of deflection. The beam 1220 is able to deflect radially inwardly/outwardly when the distal end 1204 comes into contact with the proximal end of the nail 1202. The beam 1220, in this embodiment, further includes an increased thickness flange 1222 extending across the width of the beam 1220 at a distal end thereof. The increased thickness flange 1222 is dimensioned to be removably housed within a cavity 1224 on the nail 1202 with a snap-fit engagement. The beam 1220 is positioned at one of the rounded outwardly extending points 1215 of recessed portion 1216, creating an asymmetrical shape to prevent the user from inserting the insertion handle 1200 into the nail 1202 in the wrong orientation. Specifically, the beam 1220 is substantially rectangular along a plane that is perpendicular to the longitudinal axis of the insertion handle 1200 so that the insertion handle 1200 can only be inserted into the nail 1202 when the beam 1220 is aligned with a cavity 1228 on the nail 1202. In an exemplary embodiment, each of the six points may include guiding chamfers 1240. That is, the distal edges of each of the six points may include right-angled cut-aways to make a symmetrical sloping edge, facilitating insertion of handle 1200 and reducing nicking damage to both of the components.

The nail 1202 of this embodiment, as described above has an interior surface with a hexalobular geometry matching the external geometry of the recessed portion 1214. Specifically, the inner surface in this embodiment has five rounded portions 1232 and a sixth substantially flat portion 1234 shaped to engage the beam 1220. The nail 1202 also includes a cavity 1224 on the flat portion 1234 sized and shaped to removably house the increased thickness flange 1222 of the beam 1220 with a snap-fit engagement creating an audible clicking sound indicating to the user that the insertion handle 1000 and the nail 102 are correctly aligned axially and locked together. Thus, when the insertion handle 1200 is positioned over the nail 1202 in a desired orientation, the beam 1220 snap-fits into the cavity 1224 eliminating the need for a user to manually hold the nail 1202 in place while the connecting screw 150 is inserted into the channel 1212 of the insertion handle 1200. In another embodiment, shown in FIG. 17, the cavity 1236 may extend through the wall of the nail 1202 from the inner surface to the outer surface.

Figure 20:
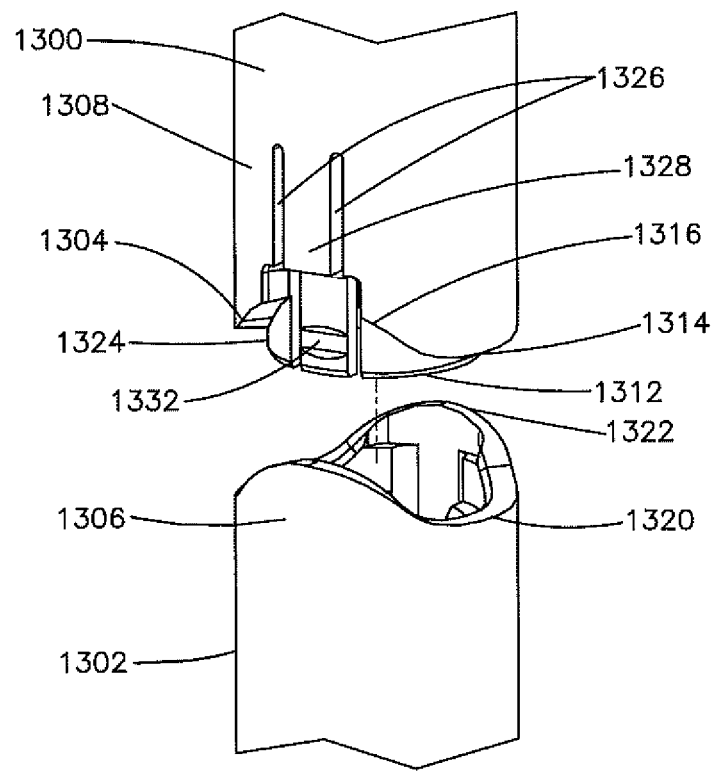
FIG. 20 shows a perspective view of an insertion handle-to-nail interface according to a fourteenth exemplary embodiment of the present disclosure.
Figure 21:
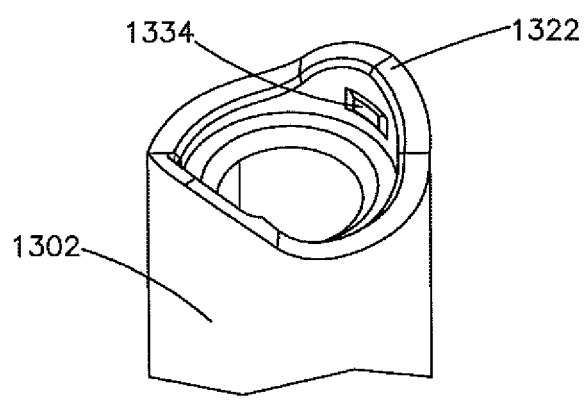
FIG. 21 shows a perspective view of an insertion handle-to-nail interface according to a fifteenth exemplary embodiment of the present disclosure.

FIGS. 20-21 depict an insertion handle-to-nail snap interface according to yet another exemplary embodiment of the invention. In this embodiment, the distal free end 1304 of the barrel 1308 of an insertion handle 1300 and the proximal end 1306 of the nail 1302 have matching profiles. Specifically, the distal end 1304 of the insertion handle 1300 includes two opposing convexly rounded portions 1314 separated by two opposing concavely rounded portions 1316. Similarly, the proximal end 1306 of the nail 1302 has two opposing concavely rounded portions 1320 configured to fit with the convex portions 1314 of the insertion handle 1300 and two convexly rounded portions 1322 configured to fit with the concave portions 1316. Each of the convex portions 1314, 1322 and the concave portions 1316, 1320 of the insertion handle 1300 and the nail 1302 in this embodiment, is substantially hemispherical. However, it will be understood that the profiles of the distal end 1304 of the insertion handle 1300 and the proximal end 1306 of the nail 1302 may have any geometry so long as they are configured to fit together. These mating profiles allow the user to easily rotationally align the insertion handle 1300 and the nail 1302 in the correct positions while also aiding in transmitting torque. Looking to the insertion handle 1300, the handle 1300 also includes a recessed portion 1324 extending distally from the distal end 1304 of the barrel 1308 and configured to be inserted into the nail 1302 to engage an inner surface thereof. The insertion handle 1300 of this embodiment further includes two parallel longitudinal slots 1326 extending from an outer surface of the handle 1300 to an inner surface thereof and defining a flexible beam 1328 therebetween. As can be seen in the figure, the slots 1326 extend proximally from the distal end of the insertion handle 1300, through the recessed portion 1324 and into a non-recessed portion 1330 of the insertion handle 1300. A length of the slots 1326 may be chosen depending on the desired range of deflection of the beam 1328. As described above, longer slots 1326 provide the beam 1328 with a greater range of deflection while shorter slots 1326 provide the beam 1328 with a smaller range of deflection. In an exemplary embodiment, the slots 1326 may be, for example, approximately 16-18 mm. The beam 1328 is able to deflect radially inwardly/outwardly relative to a longitudinal axis of the barrel 1308 when the distal end 1304 comes into contact with the proximal end of the nail 1302. The beam 1328, in this embodiment, further includes an increased thickness flange 1332 extending across the width of the beam 1328 at a distal end thereof. The increased thickness flange 1332 is dimensioned to be removably housed within a cavity 1334 on the nail 1302 with a snap-fit engagement creating an audible clicking sound indicating to the user that the insertion handle 1300 and the nail 1302 are correctly aligned axially and temporarily locked together.

The nail 1302 of this embodiment, as described above, includes the cavity 1334 on an inner surface thereof sized and shaped to removably house the increased thickness flange 1332 of the beam 1328 with a snap-fit engagement creating an audible clicking sound indicating to the user that the insertion handle 1300 and the nail 1302 are correctly aligned axially and locked together. Thus, when the insertion handle 1300 is positioned over the nail 1302 in a desired orientation, the beam 1328 snap-fits into the cavity 1334 eliminating the need for a user to manually hold the nail 1302 in place while a connecting screw 150 is inserted into the channel 1312 of the insertion handle 1300. In another embodiment, the cavity 1334 may extend through the wall of the nail 1302 from the inner surface to the outer surface.

In use, once the intramedullary nail is placed in a desired position within the bone, the user may disconnect the insertion handle from the nail by exerting a proximal axial force on the insertion handle. This force releases the mating geometries so that the insertion handle may be subsequently removed from the body. In some embodiments, the user may also wiggle the insertion handle by exerting a lateral back and forth movement to the insertion handle to release the self-retaining mechanism.

It will be understood by those skilled in the art that the insertion handles and nails of each of the described embodiments are configured to be locked together using a connecting screw 150 inserted through the channel of the insertion handle and threadedly screwed into a channel within the nail. The connecting screw 150 according to the invention includes a head 152 with a driver-engaging recess 154 and an elongated shaft 156 extending distally therefrom, a distal portion thereof including threading 158 configured to threadedly engage threading in the intramedullary nail, as those skilled in the art will understand.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. An implant insertion assembly, comprising:
an insertion handle extending from a proximal end to a distal end, the distal end including an outer wall having a radially recessed surface that defines a first shape about a perimeter thereof, the outer wall including an engagement element; and
an implant extending from a respective distal end to a respective proximal end, the proximal end of the implant including an end wall having an inner surface defining an opening, the opening of the end wall configured to receive the recessed portion of the insertion handle therein, the inner surface defining a second shape configured to extend about the first shape and define a mechanical interlock with the first shape of the outer wall of the recessed surface when the recessed surface is inserted in the opening, wherein the mechanical interlock of the first and second shapes cause torque transmission from the insertion handle to the implant, the proximal end of the implant including a receiving element in the end wall, the receiving element being separate from the mechanical interlock and positioned and oriented to receive the engagement element to removably axially lock the insertion handle to the implant.

2. The assembly of claim 1, wherein the engagement element is an increased thickness flange and the receiving element is a transverse cavity sized to receive the flange.

3. The assembly of claim 2, wherein the insertion handle further comprises a pair of longitudinal slots extending through a wall of the insertion handle from an outer surface to an inner surface thereof, the slots defining a flexible beam therebetween configured to radially deflect within a predetermined range of motion when inserted into the implant.

4. The assembly of claim 3, wherein the flexible beam is configured to create an audible clicking sound when the flange is seated in the cavity.

5. The assembly of claim 1, further comprising a connecting screw sized and shaped to be inserted through a channel extending from the proximal end to the distal end of the insertion handle and into the opening to create a stable connection between the handle and the nail.

6. The implant insertion assembly of claim 1, wherein the radially recessed surface is radially recessed with respect to a non-recessed portion of the insertion handle, such that when the outer wall of the recessed portion is inserted into the opening, the outer surface of the end wall is adjacent the non-recessed portion.

7. The implant insertion assembly of claim 1, wherein the first shape includes at least one of a first groove and a first protrusion, and wherein the second shape includes at least one of a second groove and a second protrusion, wherein at least one of the first groove and the first protrusion is configured to mechanically interlock with at least one of the second groove and the second protrusion when the recessed surface is inserted into the implant.

8. The implant insertion assembly of claim 1, wherein the receiving element comprises a slot, and wherein the engagement element comprises an extending tab that is configured to be received in the slot of the implant so as to axially lock the insertion handle to the implant.

9. An implant insertion assembly for inserting an implant, comprising:
an insertion handle having an outer wall having an outer surface that defines a recessed portion and a non-recessed portion, wherein the recessed portion is radially recessed with respect to the non-recessed portion, wherein the recessed portion has a first shape configured to mate with a proximal end of an implant to which it is to be coupled having an inner surface with a second shape that corresponds to the first shape such that the inner surface extends about the outer surface of the recessed portion, thereby defining a mechanical interlock therewith so that, when coupled to the implant, the mechanical interlock causes torque to be transmitted from the insertion handle to the implant coupled thereto, the outer wall including a coupling member that is separate from the mechanical interlock and configured to engage with the proximal end of the implant to which it is coupled to axially lock the insertion handle to the implant to which it is coupled.

10. The implant insertion assembly of claim 9, further comprising the implant.

11. The implant insertion assembly of claim 10, wherein the coupling member is configured to snap-fit with the proximal end of the implant so as to axially lock the insertion handle to the implant.

12. The implant insertion assembly of claim 11, wherein the coupling member comprises a recess, and the implant comprises a tab that is configured to snap-fit in the recess to axially lock the insertion handle to the implant.

13. The implant assembly of claim 11, wherein the coupling member comprises an undercut, and the implant defines a cantilever beam that is configured to be received in the undercut to axially lock the insertion handle to the implant.

14. The implant assembly of claim 11, wherein the coupling member comprises a ridge that is configured to be snap-fit into a groove of the implant so as to axially lock the insertion handle to the implant.

15. The implant assembly of claim 11, wherein the coupling member comprises a flange that is configured to be snap-fit within a groove of the implant, thereby axially locking the insertion handle to the implant.

16. The implant assembly of claim 11, wherein the coupling member comprises a tab sized to snap-fit in a circumferential ridge of the implant, thereby axially locking the insertion handle to the implant.

17. The implant assembly of claim 11, wherein the coupling member comprises a cutout having neck, and the proximal end of the implant comprises a tab having a width larger than the neck, such that the tab is configured to snap-fit in the cutout.

18. The implant assembly of claim 11, wherein the coupling member comprises a flexible beam having a mating feature that is configured to engage a corresponding mating feature on a radially inner surface of the implant.

19. The implant assembly of claim 11, wherein the coupling member comprises a beam having a ridge that is configured to snap-fit in a recess of the implant.

20. The implant assembly of claim 11, wherein the coupling member comprises a beam having an increased thickness flange that is dimensioned to be received in a cavity of the implant with a snap-fit engagement.

21. The implant assembly of claim 10, wherein the coupling member is configured to engage the proximal end of the implant via a friction fit.

22. The implant assembly of claim 21, wherein the coupling member comprises flexible members that are configured to project an outward lateral force against side walls of cutouts of the implant, thereby axially locking the insertion handle to the implant.

23. The implant assembly of claim 21, wherein the coupling member comprises tapered tabs that are configured to be received in cutouts of the implant.

24. The implant assembly of claim 21, wherein the coupling member comprises a tab, and the implant comprises a deflectable cantilever beam positioned adjacent a cutout that is configured to receive the tab, thereby axially locking the insertion handle to the implant.

* * * * *